United States Patent [19]

Sayo et al.

[11] Patent Number: 4,954,644
[45] Date of Patent: Sep. 4, 1990

[54] RUTHENIUM-PHOSPHINE COMPLEX

[75] Inventors: Noboru Sayo; Toshiro Takemasa; Hidenori Kumobayashi, all of Tokyo, Japan

[73] Assignee: Takasago International Corporation, Tokyo, Japan

[21] Appl. No.: 241,434

[22] Filed: Sep. 7, 1988

[30] Foreign Application Priority Data

Sep. 8, 1987 [JP] Japan .................. 62-224288

[51] Int. Cl.$^5$ .......... C07F 15/00; C07F 3/06; C07F 7/22; C07F 7/28
[52] U.S. Cl. ............................................. 556/14
[58] Field of Search ................................. 556/14

[56] References Cited

U.S. PATENT DOCUMENTS 4,691,037  9/1987  Yoshikawa et al. ............ 556/18
4,739,084  4/1988  Takaya et al. ................. 556/21

FOREIGN PATENT DOCUMENTS 0245959 11/1987 European Pat. Off. .

OTHER PUBLICATIONS

Takaya et al., *JACS*, 109, 5856–5858 (1987).
Rylander, Paul, *Hydrogenation Methods*, New York, Academic Press, Inc., 1985.
Kemp et al., *Organic Chemistry*, New York; Worth Publishers, Inc., 1980.
Noyori et al., *J. Am. Chem. Soc.*, 108, 7117–7119 (1986).
Ohta et al., *J. Org. Chem.* 52, 3174–3176 (1987).

*Primary Examiner*—Paul F. Shaver
*Attorney, Agent, or Firm*—Sughrue, Mion, Zinn, MacPeak & Seas

[57] ABSTRACT

A ruthenium-phosphine complex is disclosed, which is represented by formula (I):

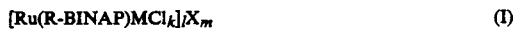

$$[Ru(R\text{-}BINAP)MCl_k]_lX_m \quad (I)$$

wherein R-BINAP represents a tertiary phosphine represented by formula (II):

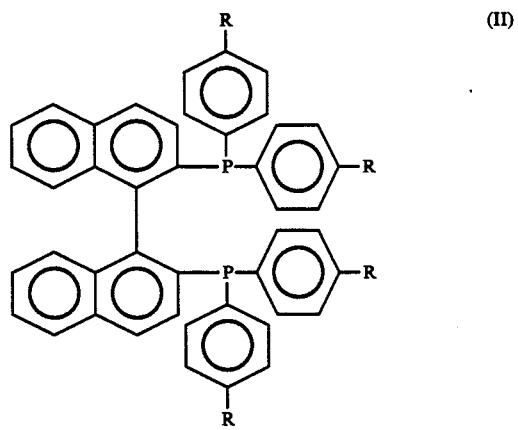

wherein R represents hydrogen atom or methyl group; M represents Zn, Al, Ti, or Sn; X represents $N(C_2H_5)_3$ or $CH_3CO_2$; in the case that X represents $N(C_2H_5)_3$, l is 2 and m is 1, and when M represents Zn, then k is 4, when M represents Al, then k is 5, and when M represents Ti or Sn, then k is 6; and in the case that X represents $CH_3CO_2$, l is 1 and m is 2, and when M represents Zn, then k is 2, when M represents Al, then k is 3, and when M represents Ti or Sn, then k is 4.

5 Claims, No Drawings

RUTHENIUM-PHOSPHINE COMPLEX

FIELD OF THE INVENTION

The present invention relates to a ruthenium-phosphine complex useful as a catalyst for various organic synthesis reactions, particularly asymmetric hydrogenation reaction.

BACKGROUND OF THE INVENTION

Hitherto, a number of transition metal complexes have been used as catalysts for organic synthesis reactions. In particular, since noble metal complexes are stable and easy in handling though they are expensive, there have been reported a number of synthesis researches using them as catalysts. In particular, there have been a number of reports on asymmetric catalysts used in asymmetric syntheses, i.e., asymmetric isomerization reaction or asymmetric hydrogenation reaction. Among them, especially metal complexes formed between metallic rhodium and an optically active tertiary phosphine are well known as catalysts for the asymmetric hydrogenation reaction. Such complexes typically include a rhodium-phosphine catalyst using 2,2'-bis(diphenylphosphino)-1,1'-binaphthyl (hereinafter abbreviated as "BINAP") as a ligand as disclosed in JP-A-55-61937. (The term "JP-A" as used herein means an "unexamined published Japanese patent application".).

On the other hand, known ruthenium complexes, though there are not so many reports as compared with rhodium complexes, include those having BINAP or 2,2'-bis(di-p-tolylphosphino)-1,1'-binaphthyl (hereinafter abbreviated as "T-BINAP") as a ligand, e.g., $Ru_2Cl_4(BINAP)_2(NEt_3)$ (wherein Et represents an ethyl group, hereinafter the same) and $Ru_2Cl_4(T-BINAP)_2(NEt_3)$, as reported in Ikariya et al., *J. Chem. Soc., Chem. Commun.*, pp. 922 (1985). Further, asymmetric hydrogenation reactions of allyl alcohol and of isoquinoline-type alkaloid using $Ru(CH_3CO_2)(BINAP)$ as a ruthenium complex are reported in Noyori et al., *J. Am. Chem. Soc.*, 109, pp. 1596 (1987) and ibid., 108, pp. 7117 (1986), respectively. Moreover, $[Ru(BINAP)]X_2$ (wherein X represents $ClO_4$, $BF_6$, or $PF_6$) is reported in H. Takaya et al., *J. Org. Chem.*, 52, pp. 3174-3176 (1987) However, the state-of-the-art ruthenium complexes are not satisfactory in catalytic activity as well as durability.

Although metallic rhodium is a metal for excellent complex catalysts, it is limited in terms of place and quantity of production and is expensive. When used as a catalyst, it forms a large proportion in cost of the product, ultimately resulting in increase in cost of the final commercial products. While metallic ruthenium is cheaper than rhodium and appears promising as a catalyst for industrial application, it still has problems in its activity to cope with precision reactions and its range of application. Therefore, it has been keenly demanded to develop a catalyst which is inexpensive, has high activity and durability, and catalyzes asymmetric reactions to attain high optical yields, i.e., to produce reaction products having high optical purity.

As a result of extensive investigations with the purpose of meeting the above-described industrial demand, the inventors have discovered a novel ruthenium complex having high catalytic activity, which is usable either for general syntheses when the ligand thereof is optically inactive or for asymmetric syntheses when the ligand thereof is optically active. The present invention has been completed based on this finding.

SUMMARY OF THE INVENTION

An object of the present invention is to provide a ruthenium-phosphine complex represented by formula (I):

$$[Ru(R\text{-}BINAP)MCl_k]_lX_m \quad (1)$$

wherein R-BINAP represents a tertiary phosphine represented by formula (II):

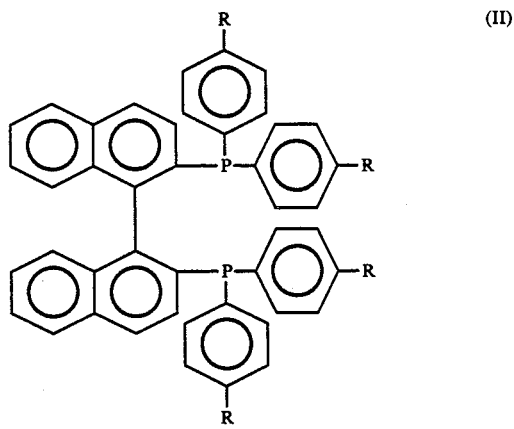

wherein R represents hydrogen atom or methyl group; M represents Zn, Al, Ti, or Sn; X represents $N(C_2H_5)_3$ or $CH_3CO_2$; in the case that X represents $N(C_2H_5)_3$, l is 2 and m is 1, and when M represents Zn, then k is 4, when M represents Al, then k is 5, and when M represents Ti or Sn, then k is 6; and in the case that X represents $CH_3CO_2$, l is 1 and m is 2, and when M represents Zn, then k is 2, when M represents Al, then k is 3, and when M represents Ti or Sn, then k is 4.

DETAILED DESCRIPTION OF THE INVENTION

The novel ruthenium-phosphine complex (I) according to the present invention can be produced by using $Ru_2Cl_4(R\text{-}BINAP)_2NEt_3$ or $Ru(CH_3CO_2)_2(R\text{-}BINAP)$ as a starting material.

The starting material, $Ru_2Cl_4(R\text{-}BINAP)NEt_3$, can be obtained by the methods as disclosed in Ikariya et al., *J. Chem. Soc., Chem. Commun.*, pp. 922 (1985) and JP-A-61-63690. That is, it can be obtained by reacting 1 mol of $[RuCl_2(COD)]_n$ (wherein COD represents cycloocta-1,5-diene, hereinafter the same), which is obtainable from reaction between ruthenium chloride and COD, with 1.2 mols of R-BINAP in a solvent (e.g., toluene or ethanol) in the presence of 4 mols of triethylamine under heating.

The thus-obtained $Ru_2Cl_4(R\text{-}BINAP)_2NEt_3$ is reacted with one member of Lewis acids selected from zinc chloride, aluminum chloride, titanium tetrachloride, and tin tetrachloride in a solvent such as methylene chloride at a temperature of from 10° to 25° C. for a period of from 2 to 20 hours. Thereafter, the solvent is distilled off, and the residue is evaporated to dryness, whereby the ruthenium-phosphine complex according to the present invention can be obtained.

Another starting material, $Ru(CH_3CO_2)_2(R\text{-}BINAP)$, can be obtained by the method proposed by the inventors in European patent No. 245,959A. That is, $Ru_2Cl_4(R-BINAP)_2NEt_3$ as a starting material, which is obtained by the method as described above, is reacted with sodium acetate in an alcoholic solvent (e.g., methanol, ethanol, and t-butanol) at a temperature of from about 20° to 110° C. for a period of from 3 to 15 hours. Thereafter, the solvent is distilled off, and the desired complex is extracted with a solvent (e.g., diethyl ether or ethanol) and then evaporated to dryness to obtain a crude complex. The crude complex is further recrystallized from a solvent (e.g., ethyl acetate) to obtain a purified product.

The thus-obtained $Ru(CH_3CO_2)2(R-BINAP)$ is reacted with one member of the above-described Lewis acids in a solvent such as methylene chloride at a temperature of from 10° to 25° C. for a period of from 2 to 20 hours. Thereafter, the solvent is distilled off, and the residue is evaporated to dryness, whereby the ruthenium-phosphine complex according to the present invention can be obtained.

In the foregoing production methods, if optically active R-BINAP is used, there can be obtained the ruthenium-phosphine complex of the present invention having the corresponding optical activity.

The thus-obtained ruthenium-phosphine complex according to the present invention has excellent properties as a catalyst for asymmetric hydrogenation reaction, etc. For example, in the asymmetric hydrogenation of enamides, e.g., (Z)-N-acyl-1-(4-methoxyphenylmethylene)-3,4,5,6,7,8-hexahydroisoquinoline, with respect to an $Ru(CH_3CO_2)_2(BINAP)$ complex reported in The Chemical Society of Japan, Spring Annual Meeting, ZlIlL43, dated April 2, 1986, though the optical yield is high as 98% ee, the catalytic activity is 100 in terms of substrate/catalyst ratio. On the other hand, the ruthenium-phosphine complex according to the present invention exhibits extremely high catalytic activity so that the reaction smoothly proceeds with the complex having a concentration of from 1/300 to 1/2000 mol per mol of the substrate and that a hydrogenation product formed therefrom provides a desired product at a selectivity reaching nearly 100%. Further, the thus-produced amide has an optical purity of from 90 to 95%. Thus, the ruthenium-phosphine complex according to the present invention shows very excellent results as industrially useful catalysts.

Next, the present invention is described in detail with reference to the following Examples and Use Examples, but the present invention is not limited thereto.

EXAMPLE 1

Synthesis of $[Ru((-)-T-BINAP)SnCl_6]_2NEt_3$ (bis[ruthenium-(2,2'-bis(di-p-tolylphosphino)-1,1'-binaphthyl)-hexachlorotin]-triethylamine):

Into a 80 ml Schlenk's tube was charged 0.52 g (0.3 mmol) of $Ru_2Cl_4((-)-T-BINAP)2NEt_3$ After thoroughly purging the Schlenk's tube with nitrogen, 20 ml of methylene chloride and 0.16 g (0.6 mmol) of $SnCl_4$ were added thereto, and the mixture was stirred at room temperature for 15 hours. After completion of the reaction, the methylene chloride was distilled off under reduced pressure, and the residue was evaporated to dryness to obtain 0.68 g of dark brown $[Ru((-)-T-BINAP)SnCl_6]_2NEt_3$. The yield was 100%. Elemental analysis for $C_{102}H_{95}Cl_{12}NP_4Sn_2Ru_2$:

|  | P | C | H | Cl |
|---|---|---|---|---|
| Found (%) | 5.91 | 53.48 | 4.36 | 17.56 |
| Calcd. (%) | 5.33 | 52.72 | 4.12 | 18.31 |

The instrumental analysis values are as follows. That is, the $^{31}P$ nuclear magnetic resonance (hereinafter abbreviated as "$^{31}P$ NMR") spectrum was measured using a Model AM400 apparatus (a product of Bruker Inc.) at 161 MHz, with the chemical shifts being measured with 85% phosphoric acid used as an external standard. $^{31}P$ NMR $(CDCl_3)\delta$ppm: 14.14 (d, J=41.7 Hz); 62.57 (d, J=41.7 Hz)

EXAMPLE 2

Synthesis of $[Ru((-)-BINAP)AlCl_3](CH_3CO_2)_2$ ([ruthenium-(2,2'-diphenylphosphino)-1,1'-binaphthyl)trichloroaluminum]-diacetate):

Into a 80 ml Schlenk's tube was charged 0.63 g (0.75 mmol) of $Ru(CH_3CO_2)2((-)-BINAP)$. After thoroughly purging the Schlenk's tube with nitrogen, 10 ml of methylene chloride was added thereto for dissolution. Separately, 0.1 g (0.75 mmol) of $AlCl_3$ was charged into a 80 ml Schlenk's tube, and 20 ml of methylene chloride and the above-prepared methylene chloride solution of $Ru(CH_3CO_2)_2((-)-BINAP)$ were successively added thereto, followed by stirring the mixture for 15 hours. After completion of the reaction, the methylene chloride was distilled off under reduced pressure, and the residue was evaporated to dryness to obtain 0.73 g of dark brown $[Ru((-)-BINAP)AlCl_3](CH_3CO_2)_2$. The yield was 100%. Elemental analysis for $C_{48}H_{38}O_4P_2Cl_3AlRu$:

|  | P | C | H | Cl |
|---|---|---|---|---|
| Found (%) | 6.17 | 60.07 | 4.38 | 11.16 |
| Calcd. (%) | 6.35 | 59.12 | 3.93 | 10.60 |

$^{31}P$ NMR $(CDCl_3)\delta$ppm: 14.16 (d, J=41.5 Hz); 62.56 (d, J=41.5 Hz)

EXAMPLES 3 TO 16

In Examples 3 to 9, complexes were synthesized in the same manner as in Example 1 except that the types of the starting R-BINAP and Lewis acid were changed; and in Examples 10 to 16, complexes were synthesized in the same manner as in Example 2 except that the types of the starting R-BINAP and Lewis acid were changed.

The analysis values of the thus-obtained complexes are shown in Table 1.

TABLE 1

| Example No. | Compound of the Invention (Molecular Formula) | Elemental Analysis Value (%) | | | $^{31}P$ NMR (δ ppm) |
|---|---|---|---|---|---|
| | | Element | Found | Calcd. | |
| 3 | $[Ru((-)-BINAP)ZnCl_4]_2NEt_3$ | P | 6.82 | 6.31 | 14.15 (d, J = 41.6 Hz) |
| | | C | 56.94 | 57.51 | 62.58 (d, J = 41.6 Hz) |
| | | H | 4.61 | 4.06 | |
| | $C_{94}H_{79}Cl_8NP_4Zn_2Ru_2$ | Cl | 13.79 | 14.45 | |
| 4 | $[Ru((-)-BINAP)AlCl_5]_2NEt_3$ | P | 6.77 | 6.33 | 14.17 (d, J = 41.5 Hz) |
| | | C | 56.70 | 57.69 | 62.57 (d, J = 41.5 Hz) |

TABLE 1-continued

| Example No. | Compound of the Invention (Molecular Formula) | Element | Found | Calcd. | $^{31}$P NMR (δ ppm) |
|---|---|---|---|---|---|
|  |  | H | 4.36 | 4.07 |  |
|  | $C_{94}H_{79}Cl_{10}NP_4Al_2Ru_2$ | Cl | 17.62 | 18.11 |  |
| 5 | [Ru((−)-BINAP)TiCl$_6$]$_2$NEt$_3$ | P | 6.61 | 5.99 | 14.17 (d, J = 41.4 Hz) |
|  |  | C | 54.23 | 54.54 | 62.57 (d, J = 41.4 Hz) |
|  |  | H | 4.35 | 3.85 |  |
|  | $C_{94}H_{79}Cl_{12}NP_4Ti_2Ru_2$ | Cl | 19.21 | 20.55 |  |
| 6 | [Ru((−)-BINAP)SnCl$_6$]$_2$NEt$_3$ | P | 6.20 | 5.60 | 14.19 (d, J = 41.3 Hz) |
|  |  | C | 50.71 | 51.05 | 62.57 (d, J = 41.3 Hz) |
|  |  | H | 3.95 | 3.60 |  |
|  | $C_{94}H_{79}Cl_{12}NP_4Sn_2Ru_2$ | Cl | 18.78 | 19.24 |  |
| 7 | [Ru((−)-T-BINAP)ZnCl$_4$]$_2$NEt$_3$ | P | 6.16 | 5.97 | 14.15 (d, J = 41.6 Hz) |
|  |  | C | 58.31 | 59.03 | 62.59 (d, J = 41.6 Hz) |
|  |  | H | 5.07 | 4.61 |  |
|  | $C_{102}H_{95}Cl_8NP_4Zn_2Ru_2$ | Cl | 13.25 | 13.67 |  |
| 8 | [Ru((−)-T-BINAP)AlCl$_5$]$_2$NEt$_3$ | P | 6.27 | 5.99 | 14.16 (d, J = 41.5 Hz) |
|  |  | C | 58.45 | 59.20 | 62.58 (d, J = 41.5 Hz) |
|  |  | H | 4.99 | 4.63 |  |
|  | $C_{102}H_{95}Cl_{10}NP_4Al_2Ru_2$ | Cl | 16.54 | 17.13 |  |
| 9 | [Ru((−)-T-BINAP)TiCl$_6$]$_2$NEt$_3$ | P | 5.91 | 5.68 | 14.15 (d, J = 41.6 Hz) |
|  |  | C | 55.72 | 56.14 | 62.57 (d, J = 41.6 Hz) |
|  |  | H | 4.76 | 4.39 |  |
|  | $C_{102}H_{95}Cl_{12}NP_4Ti_2Ru_2$ | Cl | 19.19 | 19.50 |  |
| 10 | [Ru((−)-BINAP)ZnCl$_2$](CH$_3$CO$_2$)$_2$ | P | 6.48 | 6.33 | 14.15 (d, J = 41.5 Hz) |
|  |  | C | 58.22 | 58.94 | 62.57 (d, J = 41.5 Hz) |
|  |  | H | 3.67 | 3.92 |  |
|  | $C_{48}H_{38}Cl_2O_4P_2ZnRu$ | Cl | 6.88 | 7.25 |  |
| 11 | [Ru((−)-BINAP)SnCl$_4$](CH$_3$CO$_2$)$_2$ | P | 5.97 | 5.62 | 14.14 (d, J = 41.5 Hz) |
|  |  | C | 53.04 | 52.30 | 62.59 (d, J = 41.5 Hz) |
|  |  | H | 4.11 | 3.47 |  |
|  | $C_{48}H_{38}Cl_4O_4P_2SnRu$ | Cl | 13.40 | 12.86 |  |
| 12 | [Ru((−)-BINAP)TiCl$_4$](CH$_3$CO$_2$)$_2$ | P | 5.73 | 6.00 | 14.15 (d, J = 41.6 Hz) |
|  |  | C | 56.52 | 55.89 | 62.58 (d, J = 41.6 Hz) |
|  |  | H | 4.18 | 3.71 |  |
|  | $C_{48}H_{38}Cl_4O_4P_2TiRu$ | Cl | 13.92 | 13.75 |  |
| 13 | [Ru((−)-T-BINAP)ZnCl$_2$](CH$_3$CO$_2$)$_2$ | P | 5.63 | 5.99 | 14.13 (d, J = 41.7 Hz) |
|  |  | C | 61.21 | 60.39 | 62.57 (d, J = 41.7 Hz) |
|  |  | H | 4.87 | 4.48 |  |
|  | $C_{52}H_{46}Cl_2O_4P_2ZnRu$ | Cl | 7.31 | 6.86 |  |
| 14 | [Ru((−)-T-BINAP)AlCl$_3$](CH$_3$CO$_2$)$_2$ | P | 5.76 | 6.01 | 14.14 (d, J = 41.4 Hz) |
|  |  | C | 61.23 | 60.56 | 62.55 (d, J = 41.4 Hz) |
|  |  | H | 5.08 | 4.50 |  |
|  | $C_{52}H_{46}Cl_3O_4P_2AlRu$ | Cl | 10.66 | 10.31 |  |
| 15 | [Ru((−)-T-BINAP)SnCl$_4$](CH$_3$CO$_2$)$_2$ | P | 5.21 | 5.35 | 14.16 (d, J = 41.3 Hz) |
|  |  | C | 54.46 | 53.91 | 62.57 (d, J = 41.3 Hz) |
|  |  | H | 4.81 | 4.00 |  |
|  | $C_{52}H_{46}Cl_4O_4P_2SnRu$ | Cl | 12.64 | 12.24 |  |
| 16 | [Ru((−)-T-BINAP)TiCl$_4$](CH$_3$CO$_2$)$_2$ | P | 5.54 | 5.70 | 14.14 (d, J = 41.5 Hz) |
|  |  | C | 57.81 | 57.42 | 62.58 (d, J = 41.5 Hz) |
|  |  | H | 4.94 | 4.26 |  |
|  | $C_{52}H_{46}Cl_4O_4P_2TiRu$ | Cl | 13.61 | 13.04 |  |

USE EXAMPLE 1

Asymmetric hydrogenation of (Z)-N-formyl-1-(4-methoxyphenylmethylene)-3,4,5,6,7,8 hexahydroisoquinoline:

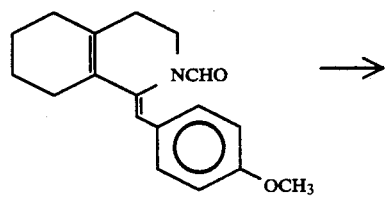

→

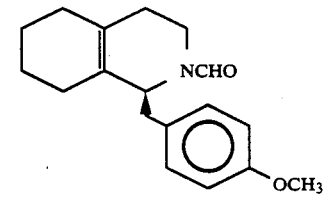

Into a Schlenk's tube which had previously been dried and purged with argon was weighed and charged 18.8 mg (0.0081 mmol) of [Ru((−)-T-BINAP)SnCl$_6$]-$_2$NEt$_3$ as a catalyst. Then, 40 ml of degassed anhydrous methanol was added thereto, and the solution was stirred in the presence of hydrogen at room temperature for 2 hours. Separately, a solution of 516 mg (1.82 mmols) of (Z)-N-formyl-1-(4-methoxyphenylmethylene)-3,4,5,6,7,8-hexahydroisoquinoline added to 20 ml of degassed anhydrous methanol was prepared. A fraction of 4.30 ml (molar ratio of substrate/catalyst = 1000/1) was taken from the catalyst solution and mixed with a substrate solution. The mixture was transferred into an autoclave and stirred at 75° C. for 47 hours under a hydrogen pressure of 35 kg/cm$^2$. After completion of the stirring, the reaction mixture was concentrated under reduced pressure and purified by silica gel column chromatography to obtain 520 mg of (+)-N-formyl-1-(4-methoxyphenylmethylene)-1,2,3,4,5,6,7,8-octahydroisoquinoline. The yield was 100%.

[α]$_D^{25}$ +22.6 (c=1.17, methanol)

After deformylation, the product was reacted with 2,3,4,6-tetra-O-acetyl-β-O-glycopyranosyl isocyanate and then subjected to reversed phase HPLC analysis to determine the optical yield. Thus, the optical yield was found to be 98% ee.

The respective spectral data are given below.

$^1$H NMR (400 MHz, CDCl$_3$)δ ppm: 1.68 (m, 4H), 1.90 (m, 4H), 2.20 (m, 2H), 2.64 (dd, J=10.4, 13.9 Hz, 0.6H), 2.90 (m, 2.4H), 3.31 (dd, J=6.6, 12.9 Hz, 0.4H), 3.58 (d, J=9.9 Hz, 0.6H), 3.77 (s, 3H), 4.37 (dd, J=6.7, 12.9 Hz, 0.6H), 4.68 (broad s, 0.4H), 6.80 (m, 2H), 6.99 (m, 0.6H), 7.05 (m, 0.4H), 7.39 (s, 0.6H), 7.92 (s, 0.4H)

$^{13}$C NMR (100 MHz, CDCl$_3$)δ ppm: 22.7, 22.8, 22.9, 27.7, 29.7, 30.0, 30.8, 33.4, 36.3, 37.6, 40.4, 53.2, 55.2, 60.4, 60.8, 113.6, 114.1, 127.77, 127.84, 128.9, 129.8, 130.0, 130.2, 130.4, 158.2, 158.4, 160.8, 161.1

UV (CH$_3$OH) nm: 220, 277, 284

MS: m/e 285

USE EXAMPLES 2 TO 16

Using each of the ruthenium-phosphine complexes obtained in Examples 2 to 16, the asymmetric hydrogenation reaction of (Z)-N-formyl-1-(4-methoxyphenylmethylene)- 3,4,5,6,7,8-hexahydroisoquinoline was carried out in the same reaction procedures as in Use Example 1 to produce (+)-N-formyl-1-(4-methoxyphenylmethylene)-1,2,3,4,5,6,7,8-octahydroisoquinoline. The results are shown in table 2.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex of formula (I):

wherein R-BINAP is a tertiary phosphate of formula (II):

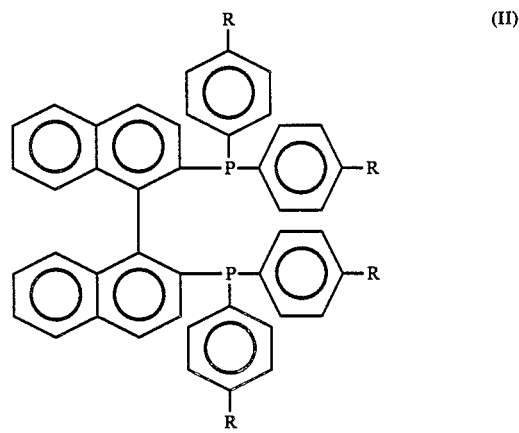

wherein R is the same and is hydrogen atom or methyl group; M is a Lewis acid selected from ZnCl$_2$, AlCl$_3$, TiCl$_4$, and SnCl$_4$; X is N(C$_2$H$_5$)$_3$ or CH$_3$CO$_2$; in the same case that X is N(C$_2$H$_5$)$_3$, then k is 2, m is 2, and n is 1; and in the case that X CH$_3$CO$_2$, then k is 0, m is 1, and n is 2.

2. A ruthenium-phosphine complex of formula (III):

TABLE 2

| Use Example No. | Compound of the Invention | Substrate/ Catalyst (mol/mol) | Hydrogen (kg/cm$^2$) | Temperature (°C.) | Time (hr) | Conversion (%) | Optical Yield (% ee) |
| --- | --- | --- | --- | --- | --- | --- | --- |
| 2 | [Ru((−)-BINAP)ZnCl$_4$]$_2$NEt$_3$ | 500 | 50 | 55 | 50 | 90 | 97 |
| 3 | [Ru((−)-BINAP)AlCl$_5$]$_2$NEt$_3$ | 1000 | 50 | 55 | 30 | 95 | 97 |
| 4 | [Ru((−)-BINAP)SnCl$_6$]$_2$NEt$_3$ | 1000 | 35 | 75 | 25 | 98 | 98 |
| 5 | [Ru((−)-BINAP)TiCl$_6$]$_2$NEt$_3$ | 1000 | 50 | 55 | 40 | 92 | 95 |
| 6 | [Ru((−)-T-BINAP)ZnCl$_4$]$_2$NEt$_3$ | 500 | 50 | 55 | 48 | 91 | 96 |
| 7 | [Ru((−)-T-BINAP)AlCl$_5$]$_2$NEt$_3$ | 1000 | 50 | 75 | 28 | 93 | 97 |
| 8 | [Ru((−)-T-BINAP)TiCl$_6$]$_2$NEt$_3$ | 1000 | 50 | 55 | 39 | 91 | 97 |
| 9 | [Ru((−)-BINAP)ZnCl$_2$](CH$_3$CO$_2$)$_2$ | 300 | 50 | 55 | 47 | 85 | 94 |
| 10 | [Ru((−)-BINAP)AlCl$_3$](CH$_3$CO$_2$)$_2$ | 1000 | 50 | 65 | 32 | 91 | 94 |
| 11 | [Ru((−)-BINAP)SnCl$_4$](CH$_3$CO$_2$)$_2$ | 1000 | 50 | 75 | 23 | 93 | 96 |
| 12 | [Ru((−)-BINAP)TiCl$_4$](CH$_3$CO$_2$)$_2$ | 500 | 50 | 55 | 38 | 89 | 95 |
| 13 | [Ru((−)-T-BINAP)ZnCl$_2$](CH$_3$CO$_2$)$_2$ | 300 | 50 | 55 | 48 | 87 | 93 |
| 14 | [Ru((−)-T-BINAP)AlCl$_3$](CH$_3$CO$_2$)$_2$ | 1000 | 50 | 75 | 29 | 90 | 94 |
| 15 | [Ru((−)-T-BINAP)SnCl$_4$](CH$_3$CO$_2$)$_2$ | 1000 | 50 | 75 | 24 | 92 | 97 |
| 16 | [Ru((−)-T-BINAP)TiCl$_4$](CH$_3$CO$_2$)$_2$ | 500 | 50 | 55 | 41 | 88 | 95 |

The present invention is to provide a novel ruthenium-phosphine complex. This complex exhibits excellent properties as a catalyst for various organic synthesis reactions, particularly asymmetric hydrogenation reaction and shows industrially superior results with respect to selective hydrogenation of olefins and catalytic activity. Further, the complex can be produced with a low production cost as compared with the conventional rhodium-based catalysts, leading to a contribution to a reduction in product price. Thus, the invention is of industrially great value.

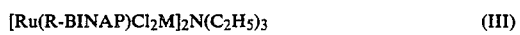

wherein R-BINAP is a tertiary phosphine of formula (II):

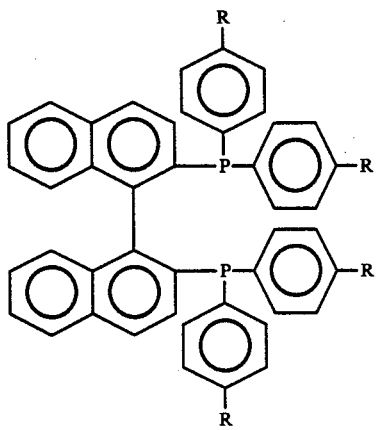

wherein R is the same and is hydrogen atom or methyl group; and M is a Lewis acid selected from $ZnCl_2$, $AlCl_3$, $TiCl_4$, and $SnCl_4$.

3. A ruthenium-phosphine complex of formula (III):

$$[Ru(R\text{-}BINAP)Cl_2M]_2N(C_2H_5)_3 \quad (III)$$

wherein R-BINAP is a tertiary phosphine of formula (II):

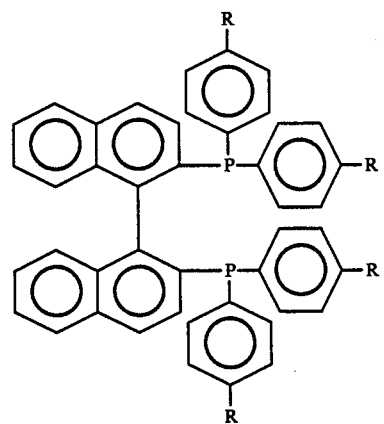

wherein R is the same and is hydrogen atom or methyl group; and M is a Lewis acid selected from $ZnCl_2$, $AlCl_3$, $TiCl_4$, and $SnCl_4$, obtained by reacting $Ru_2Cl_4(R\text{-}BINAP)_2N(C_2H_5)_3$, wherein R-BINAP is the same as defined above, with a Lewis acid selected from $ZnCl_2$, $AlCl_3$, $TiCl_4$, and $SnCl_4$ in an inert solvent at from 10° to 25° C.

4. A ruthenium-phosphine complex of formula (IV):

$$[Ru(R\text{-}BINAP)M](CH_3CO_2)_2 \quad (IV)$$

wherein R-BINAP is a tertiary phosphine of formula (II):

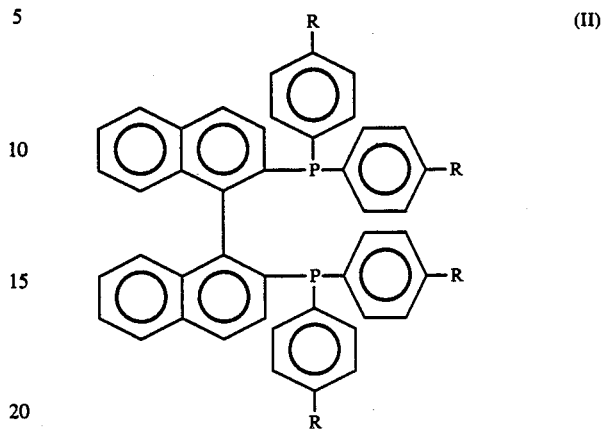

wherein R is the same and is hydrogen atom or methyl group; and M is a Lewis acid selected from $ZnCl_2$, $AlCl_3$, $TiCl_4$, and $SnCl_4$.

5. A ruthenium-phosphine complex of formula (IV):

$$[Ru(R\text{-}BINAP)M](CH_3CO_2)_2 \quad (IV)$$

wherein R-BINAP is a tertiary phosphine of formula (II):

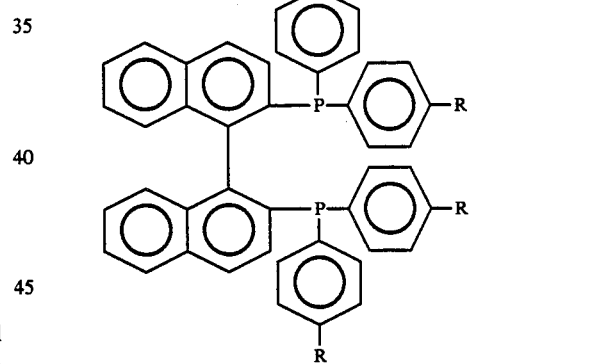

wherein R is the same and is hydrogen atom or methyl group; and M is a Lewis acid selected from $ZnCl_2$, $AlCl_3$, $TiCl_4$, and $SnCl_4$, obtained by reacting $Ru(CH_3CO_2)_2(R\text{-}BINAP)$, wherein R-BINAP is the same as defined above, with a Lewis acid selected from $ZnCl_2$, $AlCL_3$, $TiCl_4$, and $SnCl_4$ in an inert solvent at from 10° to 25° C.

* * * * *